United States Patent [19]

Shuck

[11] 4,052,885

[45] Oct. 11, 1977

[54] PORTABLE DEVICE AND METHOD FOR DETERMINING PERMEABILITY CHARACTERISTICS OF EARTH FORMATIONS

[75] Inventor: Lowell Z. Shuck, Morgantown, W. Va.

[73] Assignee: The United States of America as represented by the United States Energy Research and Development Administration, Washington, D.C.

[21] Appl. No.: 717,429

[22] Filed: Aug. 24, 1976

[51] Int. Cl.² .......................................... G01N 15/08
[52] U.S. Cl. .................................................... 73/38
[58] Field of Search ................................. 73/38, 37

[56] References Cited

U.S. PATENT DOCUMENTS

| 2,345,935 | 4/1944 | Hassler | 73/38 |
| 2,949,766 | 8/1960 | Kirkham et al. | 73/38 |
| 3,548,635 | 12/1970 | Hutchinson et al. | 73/38 |
| 3,861,196 | 1/1975 | Domenighetti | 73/38 |
| 3,889,521 | 6/1975 | Jakimowicz | 73/38 |

OTHER PUBLICATIONS

Publication: "Measurement of Air Permeability of Soil in Situ" by Evans et al., Soil Science Society Proceedings, vol. 14, 1949, pp. 65-69, 72-73.

*Primary Examiner*—Daniel M. Yasich
*Attorney, Agent, or Firm*—Dean E. Carlson; Stephen D. Hamel; Earl L. Larcher

[57] ABSTRACT

The invention is directed to a device which is used for determining permeability characteristics of earth formations at the surface thereof. The determination of the maximum permeability direction and the magnitude of permeability are achieved by employing a device comprising a housing having a central fluid-injection port surrounded by a plurality of spaced-apart fluid flow and pressure monitoring ports radially extending from the central injection port. With the housing resting on the earth formation in a relatively fluid-tight manner as provided by an elastomeric pad disposed therebetween, fluid is injected through the central port into the earth formation and into registry with the fluid-monitoring ports disposed about the injection port. The fluid-monitoring ports are selectively opened and the flow of the fluid through the various fluid ports is measured so as to provide a measurement of flow rates and pressure distribution about the center hole which is indicative on the earth formation permeability direction and magnitude. For example, the azimuthal direction of the fluid-monitoring ports in the direction through which the greatest amount of injected fluid flows as determined by the lowest pressure distribution corresponds to the direction of maximum permeability in the earth formation.

7 Claims, 3 Drawing Figures

PORTABLE DEVICE AND METHOD FOR DETERMINING PERMEABILITY CHARACTERISTICS OF EARTH FORMATIONS

The present invention relates genrally to the determination of permeability characteristics in earth formations, and more particlarly to a readily portable device for providing such determinations on exposed surfaces of the earth formations.

In various mining and drilling operations used for the recovery of hydrocarbons or commercially useable mineral values from subterranean earth formations, it has been found that knowledge of the permeability characteristics of the earth formation, especially the direction of maximum permeability and the magnitude of permeability greatly facilitates the recovery operation. For example, in a conventional underground coal mining operation, knowledge of such permeability characteristics will allow for the strategic emplacement of boreholes from the surface operation for demethanizing and dewatering the coal bed ahead of the mining operation. Also, the magnitude of the permeability of particularly useful for optimizing the placement of such boreholes. Further, the efficiency of the coal or mineral removal operation can be increased by knowing the direction of maximum permeability in the strata containing the values to be removed. For example, the fracturing of the strata by employing explosives is substantially greater when the blasting holes or bores used for accommodating the explosives are drilled in the strata along a plane generally perpendicular to the plane of maximum permeability. This benefit is derived from the fact that the planes of maximum weakness are substantially parallel to the plane of maximum permeability so that such placement of the blasting holes exposes a greater number of planes of maximum weakness to the force of the explosives.

In view of the above and other advantages realized by utilizing permeability characteristics of earth strata or formation in various mining and drilling operations, it is the primary objective or aim of the present invention to provide an easily portable self-contained mechanism for determining permeability characteristics, such as the direction of maximum permeability, the severity of the directional permeability pattern, and the magnitude of the directional permeabilities. Generally, the device for achieving this aim is a device which comprises a housing with a planar surface, a fluid-injecting passageway housing in open registry with the planar surface and a plurality of fluid-flow and/or fluid pressure-monitoring passageways, hereinafter referred to as fluid-monitoring ports, in open registry with the planar surface. The fluid-monitoring ports are spaced part apart from one another along a plane extending from the fluid-injecting passageway. Seal means are carried by the housing in an abutting relationship with the planar surface for providing a substantially fluid-tight seal with the earth formation being measured when the housing is positioned in a contiguous relationship therewith. The seal means are provided with a plurality of apertures extending therethrough in respective registry with the fluid-injecting passageway and each of the plurality of fluid-monitoring ports. A fluid reservoir means is coupled to the fluid-injecting passageway for injecting a pressurized fluid into the earth formation. Fluid flow and/or pressure measuring means are coupled to each of the fluid-monitoring ports for measuring the pressure of the injected fluid and/or the rate of flow of the injected fluid emanating from the earth formations through the fluid-monitoring ports. Thus, by measuring the inlet pressure and rate of flow and the flow or pressure distribution of the injected fluid at each of the fluid-monitoring ports at various azimuths the direction of maximum permeability and the magnitude of the permeability may be readily determined.

Other and further objects of the invention will be obvious upon an understanding of the illustrative embodiment about to be described, or will be indicated in the appended claims, and various advantages not referred to herein will occur to one skilled in the art upon employment of the invention in practice.

An embodiment of the invention has been chosen for the purpose of illustration and is not intended to be exhaustive or to limit the invention to the precise form disclosed. It is chosen and described in order to best explain the principles of the invention and their application in practical use to thereby enable others skilled in the art to best utilize the invention in various embodiments and modifications as are best adapted to the particular use contemplated.

Figure 2:
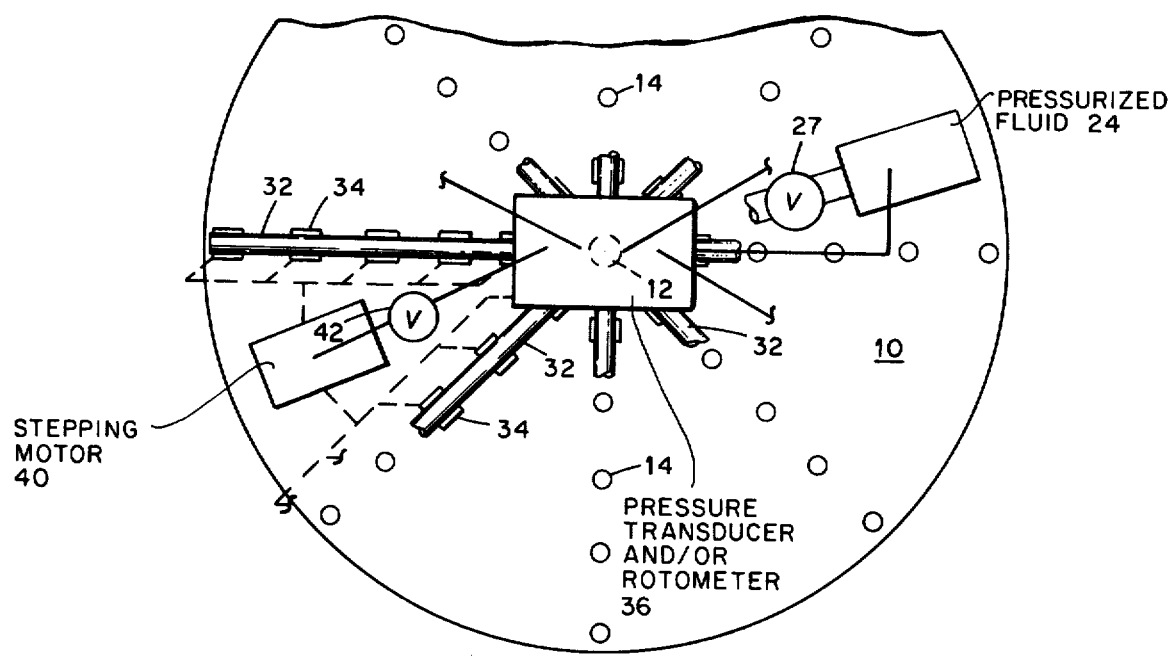
FIG. 2 is a schematic plan view, partly broken away, of the FIG. 1 embodiment showing further details of the subject device.
Figure 1:
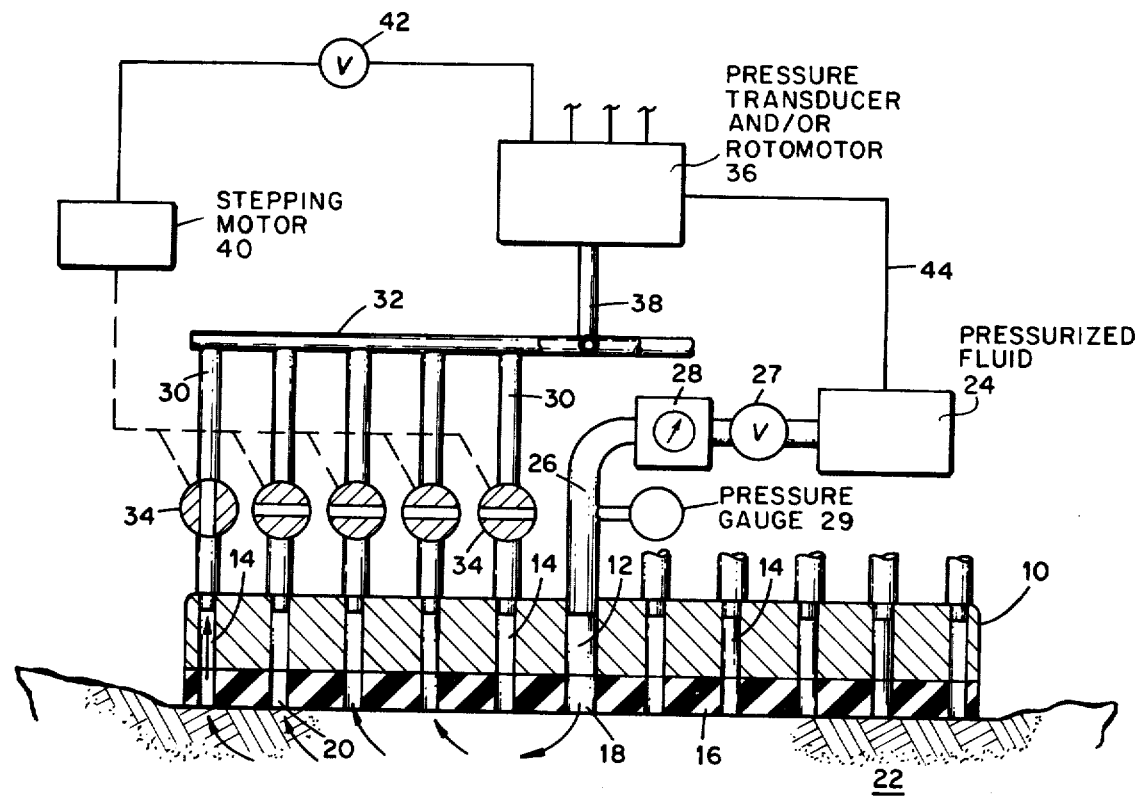
FIG. 1 is a sectional, highly schematic elevational view of one embodiment of the permeability measuring device of the present invention as it would appear in a working relationship with a planar surface of an earth formation.

With reference to FIGS. 1 and 2 of the accompanying drawing the permeability measuring device of the present invention is a readily portable self-contained device shown comprising a housing 10 of a discoidal configuration. The housing is preferably formed of a relatively heavy material, such as steel or the like, for providing sufficient weight to inhibit the lifting thereof from a horizontal surface of the earth and sufficiently rigid to assure no plate deflection during the fluid-injection operation utilized for the permeability measurements. The housing 10 as well as the components associated therewith, as will be discussed below, may be contained within a single casing for facilitating its handling and portability. The housing 10 is provided with a centrally disposed, fluid-injecting port of passageway 12 at the center or the axis of rotation thereof for injecting the fluid into the earth formation for the earth permeability measurements. Also, a plurality of fluid-monitoring ports 14 are disposed within the housing 10 and are shown arranged in a spoke-like manner corresponding to that of a wagon wheel with the fluid-injecting port at the center thereof. Each of these "spokes" or columns of ports is formed of a pluarlity of individual, radially spaced-apart fluid-monitoring ports. While each column or spoke is shown formed with five such ports, it will appear clear that any desired number of ports could be used. Also, while eight columns of the ports 14 are shown radially extending from the fluid-injecting port 12 at uniform circumferentially spaced-apart locations, it will appear clear that any suitable number of columns could be used. For example, if desired, a single column formed of a plurality of spaced-apart fluid-monitoring ports may be used to provide the function of the present invention since the housing 10 may be rotated a suitable number of degrees in azimuth after each reading so as to provide permeability measurements in substantially every azimuthal direction.

The diameter of each of the fluid-monitoring ports should be such so as to cover at least about 20 to 100 grains of the earth formation underlying each passageway. Usually a fluid-receiving passageway of a diameter of about $\frac{1}{8}$ to $\frac{1}{4}$ inch is sufficient to provide the necessary grain coverage of the underlying earth formation.

In order to provide a relatively fluid-tight coupling between the housing 10 and the earth formation in which the permeability measurements are desired, a seal means 16 is affixed in any suitable manner to the base of the housing. This seal means may be provided by an elastomeric pad of about $\frac{1}{8}$ to $\frac{1}{4}$ inch in thickness which is sufficiently soft or pliable so as to mate and conform with anomalies on the surface of the earth formation. The seal means 16 is provided with an aperture 18 in registry with the fluid-injecting port 12 as well as plurality of further apertures 20, each of which is in registry with one of the fluid-monitoring ports 14. The elastomeric seal means 16 is placed upon the surface of the earth formation 22 in which the measurements are desired. This surface may be on earth formations such as the floor or face (vertical or inclined) of a mine or a pit, or at any other surface location where such measurements are desired. In order to assure that the seal means 16 is in a fluid-tight coupling with the earth formation 22, it is preferable that the earth formation be provided with a relatively smooth planar surface, such as by employing a conventional sanding disc or the like. With the elastomeric pad positioned on this planar surface of the earth formation 22, the weight of the shousing is usually adequate to sufficiently deform the elastomeric pad so as to generally conform with any anomalies, i.e., ridges and valleys, remaining on the earth surface so as to provide the desired fluid-tight seal if the surface is horizontal. The surface plate may be hand held and pushed against a non-horizontal surface with about 5 to 50 pounds force. Alternatively, the plate can be held against any surface with a suitable bolting arrangement for long term monitoring.

The fluid-injecting port 12 is coupled to a source of pressurized fluid 24 by a conduit 26. The source of pressurized fluid may be any of suitable readily portable type. For example, a bottle of pressurized gas such as $CO_2$, nitrogen, or air, or a liquid such as distilled water, a salin solution, or any other liquid having a viscosity and/or a geochemical compatibility with the particular medium being tested, may be employed as the injection fluid for the permeability measurements. The pressure of the fluid from the source 24 of pressurized fluid may be selectively regulated through a valve 27, a flow rate measuring device, e.g., rotometer 28, and a pressure gauge 29 disposed in conduit 26, as shown, so as to provide and measure the flow characteristics of the fluid through the earth formation to gain the necessary permeability measurements. Normally, a fluid flow corresponding to that in the range of about 5 inches of water (0.05 cubic feet per minute) to about 5 psig is sufficient to provide permeability measurments in most earth formations. When the fluid is injected through port 12 into the earth formation, it in turn travels in the earth formation through the permeability planes thereof in all radial directions from the fluid-injection port. This fluid returns or emanates back to the surface and is picked up by the fluid-monitoring ports 14. These fluid-monitoring ports, in turn, convey the "picked-up" injected fluid through a conduit 30 coupled to each port 14 and to a manifold 32. A valve 34 is positioned in each conduit 30 for selectively directing the fluid received from one of the fluid-monitoring ports 14 to the manifold 32. The injected fluid entering one of the fluid-monitoring ports 14, where the valve 34 is in an open position, then flows the conduit 30 and manifold 32 into a fluid flow and pressure measuring mechanism 36. This fluid flow and pressure measuring mechanism may contain a simple strain gauge-type transducer or piezoelectric-type pressure transducer for fluid pressure measurements and rotometers, turbometers, or orifices as are well known as being capable of measuring fluid flow rates in a range of about 0.001 to 1.00 ft$^3$/minute, which will emanate from the earth formation during a permeability measurement depending upon the quantity of injected fluid and permeability of the earth formation. Alternatively, the pressure distribution under the plate under no fluid conditions through ports 14 may be achieved by employing a closed end pressure-type gauge in mechanism 36.

As shown, the fluid flow measuring device 36 receives the fluid from only a single fluid-monitoring port 14 at any one time by the selective and sequential operation of the valves 34. On the other hand, if desired, pressure measurements may be made simultaneously at all ports 14 under no-flow conditions by using pressure gauges in each conduit 30. In order to achieve the sequential flow through the fluid-receiving ports a simple stepping motor 40 may be used to sequentially open each valve for a selected period of time in a range of about 0.1 to 10 seconds for permitting the measuring means 36 to measure the fluid flow through each port 14. Preferably the valve 34 nearest to the fluid-injection port 12 is initially opened and closed and then each valve 34 in that particular column of fluid-monitoring ports as well as in the column of ports diametrically opposed thereto be sequentially opened and closed and then the valve 34 in the next column of fluid-monitoring ports circumferentially spaced therefrom be sequentially opened and closed to provide permeability measurements in another azimuth direction of the earth surface until the entire system of fluid-monitoring ports have provided the measuring means 36 with fluid so as to provide a measurement of the permeability characteristics in all directions from the housing. The stepping motor 40 may be of any desirable pneumatically or electrically operable type and of a configuration such that a single stepping motor 40 may be coupled to each of the valves 34. Alternatively, as shown, a plurality of stepping motors 40 are used with each stepping motor 40 coupled to a selected number of valves 34. In a pneumatic operation a valve 42 is shown coupled to stepping motor 40 for supplying energizing fluid to the stepping motor for a desired period of time during the permeability measurements. This valve 42 may be, in turn, operated by a stepping motor, not shown, so as to sequentially operate the various valves 42 and stepping motors associated therewith. The fluid for operating the stepping motors 40 and the stepping motors for valves, 42 if such are employed, may be readily provided by the pressurized fluid source 24 via line 44.

In a typical operation of the fluid permeability measuring device of the present invention the earth surface is initially prepared by grinding the surface to provide a relatively smooth planar surface. The housing 10 is then placed in registry therewith so as to provide a uniform fluid-tight seal between the elastomeric pad 16 and the earth surface 22. With the housing 10 in place, the valve 27 is opened to allow the pressurized fluid from source 24 to pass through the fluid-injecting port 12 into the earth formation. As the fluid from this injecting port enters this earth formation, it becomes dispersed in all azimuthal directions with the greatest flow of fluid following the plane of maximum permeability in the earth formation. As the fluid progresses through the earth formation a portion of the fluid returns to the surface 22 at locations close to be radially spaced from the fluid-injecting port 12. The fluid-monitoring ports 14 are, in turn, sufficiently spaced from this fluid-injecting port so as to be in position for receiving the injected fluid as it emanates to to the surface. As the fluid emanates from the earth formation, it is sequentially led through each of the fluid-monitoring ports into the manifold 32 and thence into the fluid flow measuring means 36. As the fluid flow is measured a simple visual readout on the measuring means 36 may be used to display the fluid flow from any given fluid-monitoring port. Thus, with the fluid-monitoring ports 14 disposed in a known azimuth, the quantity of fluid measured by fluid-measuring means 36, is indicative of the permeability characterisitics of the earth formation. More specifically, the column of fluid-monitoring ports 14 through which the greatest flow of fluid achieved is indicative of the direction of maximum permeability in the earth formation. Also, the pressure drop of the fluid received through these ports 14 is indicative of the magnitude of permeability. Thus, the present invention affords a mechanism of readily determining the direction of maximum permeability as well as a fairly accurate reading as to the extent of permeability to the earth formation. It may be desirable, after achieving an initial reading through all of the fluid-monitoring ports, to rotate the housing to a new azimuth direction and retake the fluid flow readings so as to assure that an accurate determination as to the permeability characteristics has been achieved.

Figure 3:
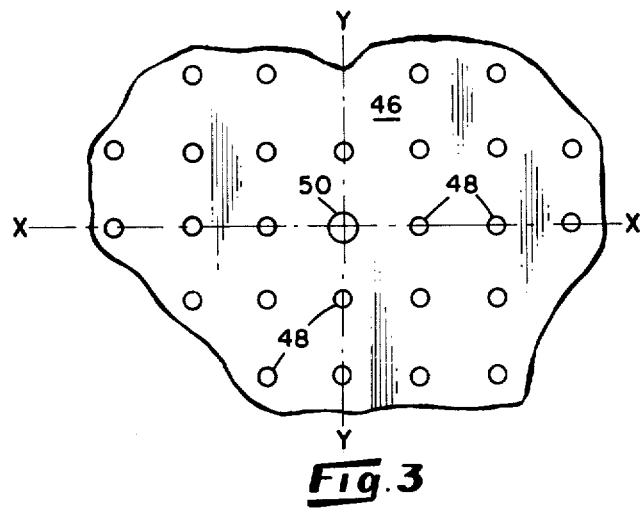
FIG. 3 is a fragmentary plan view of a further embodiment of the present invention showing the fluid-monitoring ports disposed along X and Y coordinates.

With reference to FIG. 3, there is shown another embodiment of the present invention wherein the fluid flow rate and/or fluid pressure may be measured according to a rectangular network suitable for statistical deduction, separation of local anomalies, and the detection of relatively large scale field trends. As shown, the housing 46, which corresponds to housing 10 in FIGS. 1 and 2, is provided with fluid-monitoring ports 48 arranged in a rectangular Cartesian coordinate system, i.e., the ports 48 are disposed along X and Y axes, with the central point (0,0) being at the center of the fluid-injecting port 50. This arrangement of ports 48 accommodates the use of existing numerical finite difference programs for the determination of the permeability characteristics and also facilitates statistical experimental monitoring, data reduction and data analysis for indicating total real fied directional trends by permitting the elimination of non-significant statistical values. This embodiment is operabel with a fluid-injecting and fluid-flow and/or pressure measuring arrangement similar to that of the FIGS. 1 and 2 embodiment with, of course, the conduits, manifolds, and valving suitably oriented for application with the rectangular array of fluid-monitoring ports.

It will be seen that the present invention provides a readily portable mechansim for providing permeability readings at the surface of the earth formations in mines and other locations where fluid permeability measurements are desired with such readings being achieved in a manner substantially simpler than by employing previously known mechanism so as to greatly facilitate the mining and recovery of hydrocarbons and other minerals.

What is claimed is:

1. A device for determining maximum permeability direction and magnitude of permeability of an earth formation, comprising a housing having a planar surface, a fluid-injecting passageway in said housing in open registry with said surface, a plurality of fluid-monitoring ports in said housing in open registry with said surface, with said fluid-monitoring ports being spaced apart from one another and said fluid-injecting passageway in a predetermined array, seal means carried by said housing in an abutting relationship with said surface for providing a substantially fluid-tight seal with said earth formation when said housing is positioned in a contiguous relationship with a surface of said earth formation, said seal means having a plurality of apertures therethrough in respective registry with said fluid-injecting passageway and each of said plurality of fluid-monitoring ports, a fluid reservoir means coupled to said fluid-injecting passageway for injecting a fluid into said earth formation, at least one of a fluid flow measuring means and a fluid pressure measuring means, and means selectively coupling said at least one of said measuring means to each of the fluid-monitoring ports for selectively measuring said at least one of pressure and flow characteristics in a selected manner of the injected fluid emanating from said earth formations into said fluid-monitoring ports.

2. A device for determining permeability characteristics of an earth formation as claimed in claim 1, wherein valve means are disposed intermediate said fluid-monitoring ports and said fluid flow measuring means, and wherein said valve means are selectively actuated fo sequentially placing said fluid-monitoring ports in registry with said at least one fluid pressure and fluid flow measuring means.

3. A device for determining permeability characteristics of an earth formàtion as claimed in claim 1, wherein said housing is rotatable on said surface of the earth formation, wherein said fluid-injecting passageway extends through the rotational axis of said housing, said fluid-monitoring ports are disposed in a plurality of columns each containing a plurality of fluid-monitoring ports and radially extending from said fluid-injecting passageway, and wherein the columns of fluid-monitoring ports extend in circumferentially spaced-apart directions with respect to said axis.

4. A device for determining permeability characteristics of an earth formation as claimed in claim 3, wherein the coupling between said fluid-monitoring ports and said fluid flow measuring means comprises a manifold and a plurality of conduits each extending between said manifold and one of said fluid-monitoring ports, and wherein said valve means comprises a valve in each of said conduits.

5. A device for determining permeability characteristics of an earth formation as claimed in claim 4, wherein stepping motor means are coupled to each valve for sequentially actuating said valves so that said at least one of said fluid flow measuring means and said fluid pressure means measures fluid characteristics through only one of said fluid-monitoring ports at a time.

6. A device for determining permeability characteristics of an earth formation as claimed in claim 1, wherein said fluid-monitoring ports are disposed in a plurality of columns in a Cartesian coordinate system, and wherein said fluid-injecting passageway is at the central point of said coordinate system.

7. A method for determining maximum permeability direction and magnitude of permeability of an earth formation, comprising the steps of injecting a fluid through a central port in a housing sealingly contacting the earth formation at an exposed surface thereon, gathering said fluid as it emanates from said surface at a plurality of ports located in the housing spaced from the location of the fluid injection, and selectively measuring at least one of the the fluid flow and pressure characteristics of the fluid gathered from each of said plurality of locations for determining said maximum permeability direction and magnitude of permeability.

* * * * *